United States Patent
Steward et al.

(10) Patent No.: US 7,166,098 B1
(45) Date of Patent: Jan. 23, 2007

(54) MEDICAL ASSEMBLY WITH TRANSDUCER FOR LOCAL DELIVERY OF A THERAPEUTIC SUBSTANCE AND METHOD OF USING SAME

(75) Inventors: Jeffrey A. Steward, San Jose, CA (US); Brandon Gosiengfiao, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,548

(22) Filed: Dec. 30, 1999

(51) Int. Cl.
*A61M 31/00* (2006.01)
*A61B 17/20* (2006.01)

(52) U.S. Cl. ............ 604/508; 604/96.01; 604/22

(58) Field of Classification Search ............ 604/19–22, 604/500–501, 508–509, 96.01, 102.01–102.03, 604/103, 103.01–103.02, 103.1, 264, 523, 604/529, 915; 606/192, 194; 607/96, 97
See application file for complete search history.

(56) References Cited

U.S. PATENT DOCUMENTS

| | | | |
|---|---|---|---|
| 5,279,546 A | 1/1994 | Mische et al. ............... 604/22 |
| 5,282,785 A | 2/1994 | Shapland et al. ............ 604/21 |
| 5,286,254 A | 2/1994 | Shapland et al. ............ 604/21 |
| 5,458,568 A | 10/1995 | Racchini et al. ............ 604/19 |
| 5,569,198 A | 10/1996 | Racchini ..................... 604/96 |
| 5,618,275 A * | 4/1997 | Bock ........................ 604/290 |
| 5,628,730 A | 5/1997 | Shapland et al. ............ 604/21 |
| 5,725,494 A | 3/1998 | Brisken ...................... 604/22 |
| 5,735,811 A * | 4/1998 | Brisken ...................... 604/22 |
| 5,800,392 A | 9/1998 | Racchini ..................... 604/96 |
| 5,807,306 A | 9/1998 | Shapland et al. ............ 604/21 |
| 5,846,218 A | 12/1998 | Brisken et al. .............. 604/22 |
| 6,117,101 A * | 9/2000 | Diederich et al. ........... 604/22 |
| 6,296,619 B1 * | 10/2001 | Brisken et al. .............. 604/22 |

* cited by examiner

*Primary Examiner*—LoAn H. Thanh
(74) *Attorney, Agent, or Firm*—Squire, Sanders & Dempsey L.L.P.

(57) ABSTRACT

A medical assembly is used to deliver a therapeutic substance to a treatment area. The medical assembly comprises a catheter having a distal end and a proximal end, a transducer supported by at least a portion of the distal end of the catheter assembly, and a delivery lumen mounted on the catheter for delivery of a therapeutic substance. Support for the transducer is provided at a preselected number of anchoring points, wherein an inner surface of the transducer is positioned at a preselected distance from an outer surface of the catheter. The preselected distance defines a gap that is occupied by a low density material such as a gas which reflects acoustic pressure waves directed toward the gap by a transducer when a voltage is applied to the transducer. The reflected pressure wave increases the energy in the system, enhancing transport of therapeutic substances from the delivery lumen to the surrounding tissues and/or cells to be treated. The medical assembly may optionally be used in conjunction with both macroporous and microporous balloons. The medical assembly may optionally be modified so that a plurality of transducers are used, wherein the distal end of a transducer is positioned at a preselected distance from the proximal end of an adjacent transducer.

7 Claims, 4 Drawing Sheets

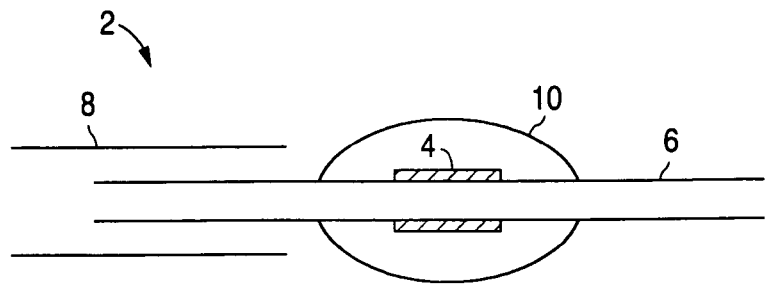
FIG. 1
(PRIOR ART)
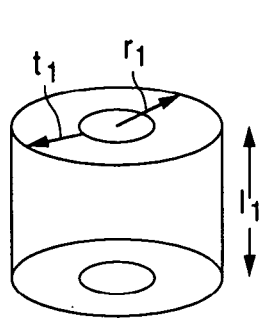 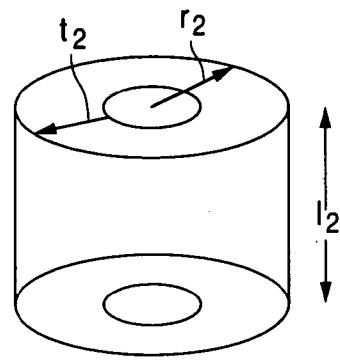
FIG. 2A          FIG. 2B
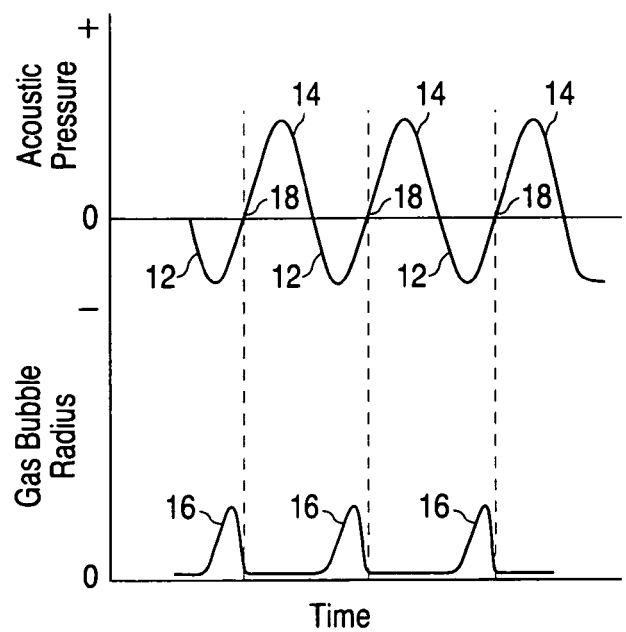
FIG. 3

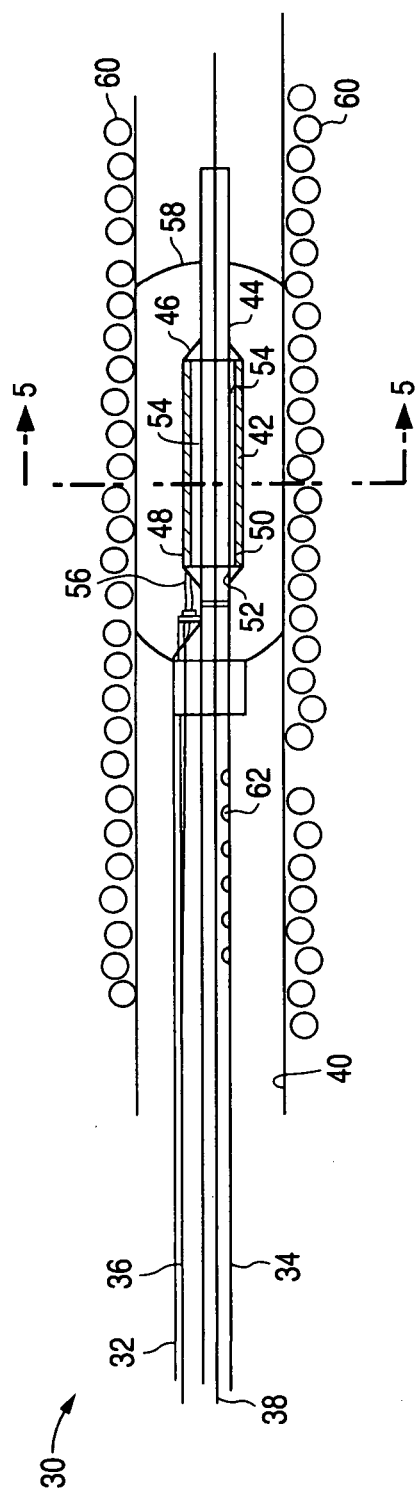
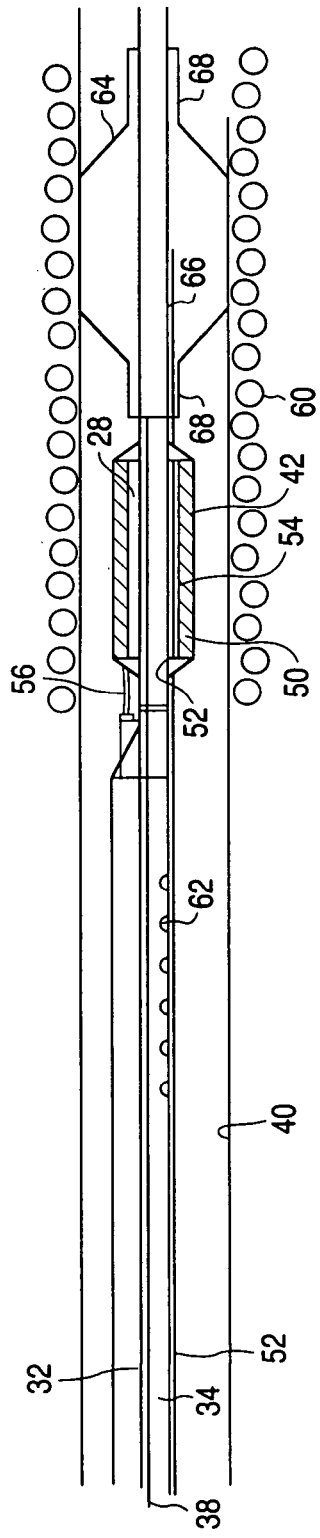
FIG. 5A
FIG. 5B

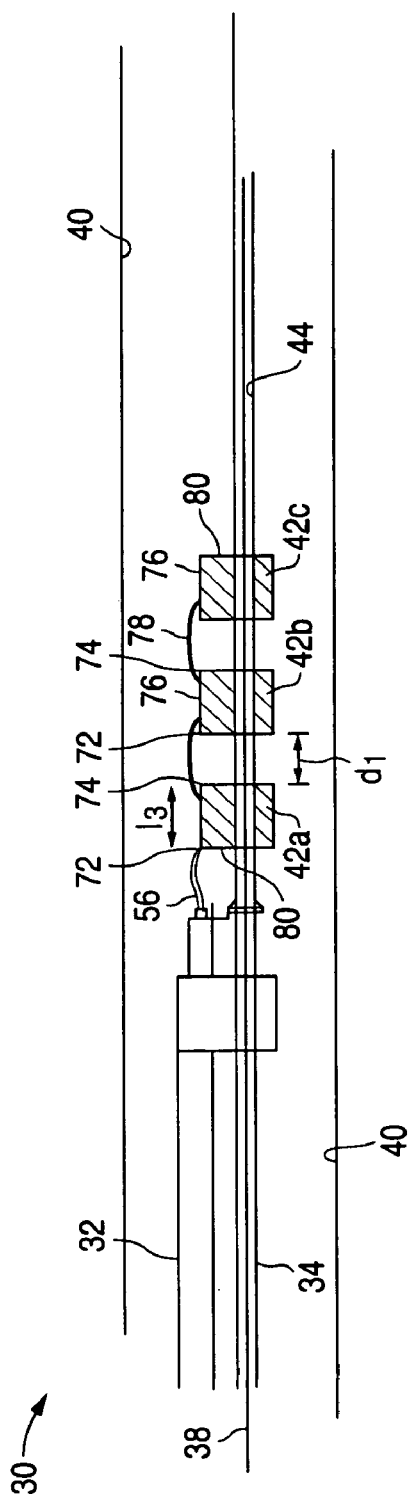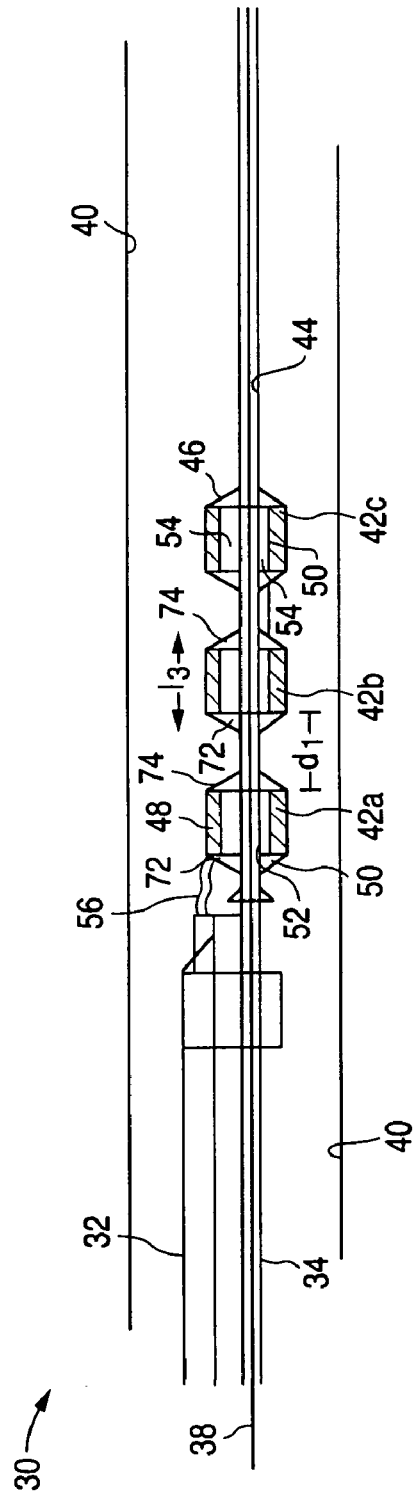

MEDICAL ASSEMBLY WITH TRANSDUCER FOR LOCAL DELIVERY OF A THERAPEUTIC SUBSTANCE AND METHOD OF USING SAME

BACKGROUND OF THE INVENTION

1. Field of the Invention

The present invention relates generally to an apparatus for and method of delivery of therapeutic substances. More specifically, the invention is directed to a medical assembly including a catheter having a transducer, which provides the driving force for transport of therapeutic substances into a tissue target area when an electrical signal with appropriate characteristics is applied to the transducer. A method of using the medical assembly is also described.

2. Description of the Related Art

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radically compress the atherosclerotic plaque of the lesion against the inner wall of the artery to dilate the arterial lumen. The balloon is then deflated to a smaller profile to allow the catheter to be withdrawn from the patient's vasculature.

In treating the damaged vascular tissue and to deter thrombosis and restenosis, therapeutic substances are commonly administered systemically. For example, anticoagulants, antiplatelets and cytostatic agents are commonly used to prevent thrombosis of the coronary lumen, to inhibit development of restenosis, and to reduce post-angioplasty proliferation of the vascular tissue, respectively.

Systemic administration of such therapeutic substances in sufficient amounts to supply an efficacious concentration to the local treatment site often produces adverse or toxic side effects for the patient. Accordingly, local delivery is a preferred method of treatment since smaller total levels of medication are administered in comparison to systemic dosages, but the medication is concentrated at a specific treatment site. Local delivery thus produces fewer side effects and achieves more effective results.

However, even with most local drug delivery devices used in conjunction with PTCA, a large majority of the drug does not go into the artery itself, but is flushed downstream and away from the target treatment area. Therefore, improvements in the efficiency of delivery of therapeutic substances into coronary arteries continue to be sought.

Phonophoresis, also referred to as sonophoresis, is a transport mechanism that uses ultrasonic or high frequency sound waves to drive an agent into the tissues of the passageway and, if desired, to increase cellular uptake. These sound waves may be produced by, for example, a transducer. Phonophoresis has several advantages over other drug delivery techniques, such as porous balloons and iontophoresis, including the ability to achieve greater penetration into the internal body tissue, and the capacity of not being limited to ionic charged forms of the agent. U.S. Pat. No. 5,800,392 to Racchini is an example illustrating the use of phonophoresis for the local delivery of a therapeutic substance or substances.

Phonophoresis is also advantageous because it increases tissue temperature, tissue permeability (i.e., permeability of the extracellular matrix), capillary permeability, and cellular permeability. These factors enhance intra-tissue transport of an agent, and cause vasodilation/relaxation, which may be beneficial in vascular applications of the present invention.

FIG. 1 illustrates a common commercial design of a phonophoresis device 2, which includes a transducer 4 mounted on a lumen 6 of a catheter 8. Transducer 4 may be disposed within a balloon 10. A disadvantage associated with this design includes the absorption of ultrasonic sound waves by lumen 6 upon which transducer 4 is mounted, thus reducing the total energy available for transporting therapeutic substances. To increase the effectiveness of the performance of the transducer, the intensity of the operating power of the transducer has to be increased. However, higher intensity operating power generates greater heat which can irreparably damage the tissues which are being treated. Accordingly, there is a constant tradeoff between increasing the performance of transducer 4 and maintaining the heat at a temperature at which tissues cannot be damaged. Additionally, transducer 4 is made from an inflexible ceramic material which significantly limits the ability of catheter 8 to flexibly navigate and maneuver through the vasculature of the subject.

What is needed is an improved transducer design which allows an operator to increase the intensity of the ultrasonic field generated by the transducer, thereby increasing the diffusion rate of therapeutic substances during phonophoresis, without excessively increasing the production of heat. Further desirable characteristics include, but are not limited to, increased efficiency of the phonophoresis process, and a transducer that can be more easily navigated through the tortuous vasculature of a subject.

SUMMARY OF THE INVENTION

In accordance with an embodiment of the present invention, a medical assembly comprises a catheter having a distal end and a proximal end, a transducer supported by at least a portion of the distal end of the catheter assembly, and a delivery lumen mounted on the catheter. The delivery lumen extends from the distal end of the catheter to the proximal end of the catheter for the delivery of a therapeutic substance therethrough. Support for the transducer is provided at a preselected number of anchoring points, wherein an inner surface of the transducer is positioned at a preselected distance from an outer surface of the catheter assembly. This distance defines a gap between the outer surface of the catheter and the inner surface of the transducer.

In another embodiment, a plurality of transducers are supported by at least a portion of the distal end of the catheter assembly. Each transducer has a proximal end and a distal end, wherein the distal end of a first transducer is positioned at a preselected distance from the proximal end of a second transducer.

In another embodiment, a plurality of transducers is supported by at least a portion of the distal end of the catheter assembly at a preselected number of anchoring points, wherein an inner surface of each transducer is positioned at a preselected distance from an outer surface of the catheter. Each transducer has a proximal end and a distal end, wherein the distal end of the first transducer is positioned at a preselected distance from the proximal end of a second transducer.

In yet another embodiment, the transducers in any of the embodiments above can be disposed within a balloon.

In yet another embodiment, a sealing balloon can be provided distally from both the intended treatment area and the transducers in any of the embodiments above.

In accordance with another aspect of the invention, a method for local delivery of a therapeutic substance to an internal body tissue target area includes providing a catheter having a distal end and a proximal end, a delivery lumen extending from the distal end to the proximal end of the catheter for delivery of a therapeutic substance therethrough, and a transducer supported by at least a portion of the distal end of the catheter at a preselected number of anchoring points. The inner surface of the transducer is positioned at a preselected distance from an outer surface of the catheter. The catheter is positioned proximate to the internal body tissue target area, a therapeutic substance is caused to elute from the delivery lumen at the distal end of the catheter, and an electrical signal is transmitted to the transducer.

BRIEF DESCRIPTION OF THE DRAWINGS

Embodiments of the present invention may be better understood, and its numerous objects, features, and advantages made apparent to one of ordinary skill in the art by referencing the accompanying drawings.

FIG. 1 illustrates a common commercial design of a phonophoresis device.

FIGS. 2A and 2B illustrate a tubular piezoelectric crystal in accordance with one embodiment of the present invention.

FIG. 3 is a graph illustrating the relationship between expansion and compression waves which occur when sound passes through a liquid, and the formation, growth and rapid collapse of gas bubbles in a liquid under acoustic pressure.

FIG. 5A is a partial cross-sectional view of one embodiment of a catheter assembly having a transducer disposed at the distal end of the catheter assembly, wherein an inner surface of the transducer is positioned at a preselected distance from the outer surface of the catheter. The transducer is disposed within a balloon.

FIG. 5B is a partial cross-sectional view of one embodiment of a catheter assembly, wherein a sealing balloon is positioned distal to the transducer, wherein an inner surface of the transducer is positioned at a preselected distance from the outer surface of the catheter.

FIG. 7 is a partial cross-sectional view of one embodiment of a catheter assembly having a plurality of transducers disposed at the distal end of the catheter assembly, wherein an inner surface of each transducer is mounted directly on the shaft of the catheter, and wherein the distal end of a first transducer is positioned at a preselected distance from the proximal end of the second transducer.

FIG. 8 is a partial cross-sectional view of one embodiment of a catheter assembly having a plurality of transducers disposed at the distal end of the catheter assembly, wherein an inner surface of each transducer is positioned at a preselected distance from the outer surface of the catheter, and wherein the distal end of each transducer is positioned at a preselected distance from the proximal end of an adjacent transducer.

The use of the same reference numbers in different drawings indicates similar or identical items.

DETAILED DESCRIPTION

Figure 4:
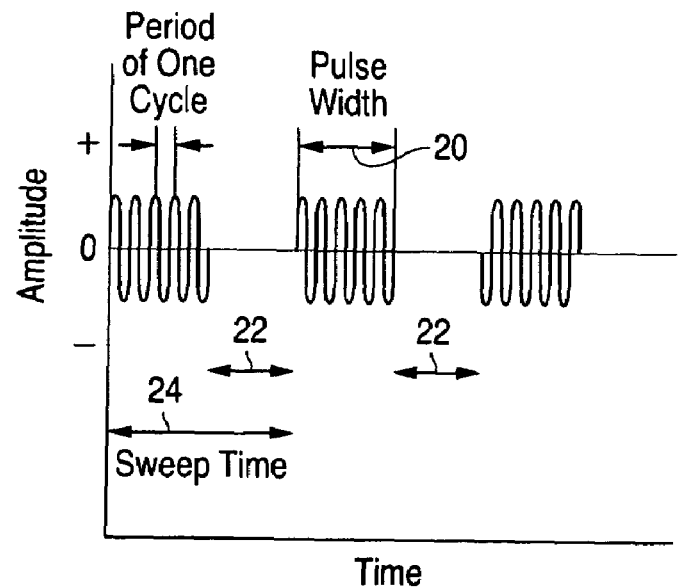
FIG. 4 illustrates an electrical signal waveform and its associated parameters that may be used when practicing a method in accordance with various embodiments of the present invention.

A method for generating ultrasonic or high energy sound waves is through the application of a signal to an ultrasonic transducer or piezoelectric crystal, which causes a mechanical distortion and vibration of the crystal. The mechanical strain produced in the structure of the crystal under electric stress is called the converse piezoelectric effect. FIG. 2A illustrates a tubular piezoelectric crystal which can be used in phonophoresis therapy. The piezoelectric crystal has an axial length $l_1$, a radius $r_1$, and a wall thickness $t_1$. Each dimension of the piezoelectric crystal has an associated resonant frequency value. Under the influence of an applied signal, the piezoelectric crystal expands and assumes a new axial length $l_2$, a new radius $r_2$, and a new wall thickness $t_2$, as illustrated in FIG. 2B. The removal of the applied voltage causes the crystalline structure to contract and return to the original dimensions of $l_1$, $r_1$ and $t_1$.

Vibration of the crystal can be induced by driving the piezoelectric crystal with an oscillating signal, for example, a signal having an amplitude of 125 to 250 volts. Thus, the crystal converts electrical signals to mechanical motion. To optimize the vibration of the crystal, the frequency of the oscillating signal should be approximately equal to the mechanical resonance frequency of the crystal, usefully equal to the resonance frequency of the radial dimension $r_1$.

The exact mechanism by which phonophoresis enhances penetration of the therapeutic substance into the tissues of the walls of a blood vessel and the cytoplasms of the cells which make up the tissues is not completely understood. In addition to the acoustic pressure and an increase in tissue temperature caused by the vibration of the crystal, it is proposed that acoustic cavitation which causes microstreaming, also plays a role in enhancing therapeutic substance penetration. Acoustic cavitation is dependent on factors such as the geometric structure of the crystal, the driving signal applied to the crystal, and the medium through which the ultrasound waves travel.

Acoustic cavitation occurs when a liquid is subjected to a sufficiently intense sound or ultrasound, e.g., sound with frequencies of about 20 kHz to 10 MHz. As illustrated in the upper portion of the graph in FIG. 3, sound passing through a liquid is composed of expansion, negative pressure waves 12 and compression, positive pressure waves 14. Gas bubbles inherently suspended in the fluid are pulled out of suspension by applying a negative acoustic pressure of a sufficient magnitude. The gas bubble radius, as illustrated by curve 16, continues to increase in size as the magnitude of the negative acoustic pressure increases. When the magnitude of the acoustic pressure becomes greater than zero, as illustrated by points 18, gas bubbles collapses. The development and collapse of gas bubbles is known as acoustic cavitation. The collapse of bubbles causes turbulent fluid zones, a phenomenon referred to as microstreaming. Microstreaming enhances transport of therapeutic substances into the vascular tissue matrix and the cells.

Evidence exists to suggest that ultrasound will cause a therapeutic substance to physically be transported into a cell cytoplasm under conditions where pressure alone does not transport the drug. The high energy state associated with acoustic cavitation may temporarily create a hole in the cell wall, allowing a therapeutic substance to actually enter the cell. It is contemplated by one of ordinary skill in the art that physical penetration of an agent or a therapeutic substance into the cytoplasm of a cell could be used to perform cell-based therapies, such as gene therapy.

The driving signal, which is comprised of frequency, amplitude, duty cycle, and sweep time, can be controlled to adjust crystal driving conditions. The activated crystal generates acoustic pressure waves that oscillate at frequencies greater than 20,000 times per second, i.e., greater than 20 kHz. Driving signal frequencies between 20 kHz and 3 MHz are useful for delivering therapeutic substances into the cytoplasm of the cells. Slightly higher frequencies, e.g., between 200 kHz and 8 MHz, typically with an upper limit of 10 MHz, are useful for penetration of therapeutic substances into the tissues of the passageway.

Generally, electrical signals with greater amplitude create greater vibration which enhances diffusion of the drug into the target tissues and cells. The highest value of the amplitude that can be achieved is limited by the physical characteristics of the crystal. Excessive amplitudes cause crystals to fracture under the mechanical strain of vibration. In addition, the more power that is applied to the crystal, the more heat that is developed. Excessive heat can irreparably damage the tissue being treated.

FIG. 4 illustrates an electrical signal waveform, and its associated parameters, that can be applied to the crystal when using the apparatus in accordance with various embodiments of the present invention. Delivery of a therapeutic substance appears to be related to maximum amplitude, not time averaged amplitude (power). By pulsing the electrical drive signal, that is, transmitting an electrical signal for a period of time, the time defining the pulse width 20, followed by a quiescent period 22, wherein there is no electrical signal, before again transmitting an electrical signal, a high amplitude can be maintained while providing a relatively low total power input level. The time defining the pulse width 20, added to the quiescent period 22 is herein called the sweep time 24. The ratio of pulse width to sweep time is herein called the duty cycle.

FIG. 5A illustrates a medical assembly in accordance with an embodiment of the invention. The type of catheter assembly 30 is not of critical importance. The illustrative catheter assembly 30 includes an elongated catheter tube 36 having a guidewire/perfusion lumen 34 and a delivery/electrical lumen 32. Guidewire/perfusion lumen 34 is configured to receive guidewire 38 which is used to maneuver catheter assembly 30 through a passageway 40.

In one embodiment, a transducer 42 is supported by at least a portion of a distal portion 44 of the catheter assembly 30 at a preselected number of anchoring points 46. Transducer 42 may be a piezoelectric crystal or any other suitable material. For use in diagnostic ultrasound and delivery of therapeutic substances, the piezoelectric crystal may be formed from, for example, a lead zirconate titanate compound. Model Nos. PZT4 and PZT8, manufactured by Morgan Matroc, are considered to be "hard" materials, i.e., can withstand high levels of electrical excitation and mechanical stress, and are formed from a lead zirconate titanate compound. Transducer 42 can be defined by a hollow tubular body having an outer surface 48 and an opposing inner surface 50. Outer surface 48 and inner surface 50 can be coated conformally with perylene or a similar compound. The addition of the coating to outer surface 50 both electrically insulates the positive and negative poles of the crystal, and also isolates fluids, such as a therapeutic substance solution, from transducer 42. Anchoring points 46 are formed from medical grade adhesives. The selected choice of medical grade adhesive should be mutually compatible both with the coating and the material forming distal portion 44 of catheter assembly 30. Anchoring points 46 should act as standoffs to separate inner surface 50 of transducer 42 from an outer surface 52 of the catheter, thereby creating a gap 54.

Figure 6:
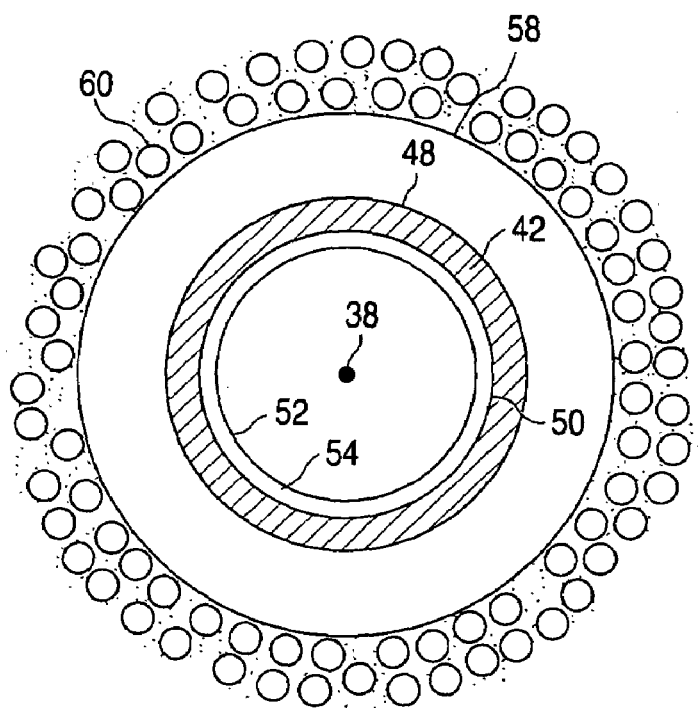
FIG. 6 is a cross-sectional view of one embodiment of a catheter assembly shown in FIG. 5A, taken in the direction of the arrows and along the plane of line 5—5 of FIG. 5A.

Gap 54 may contain any suitable low density material, including gaseous substances such as ambient air, oxygen, nitrogen, helium, an open-cell polymeric foam, a closed-cell polymeric foam, and other similar polymeric materials and mixtures thereof. When an electrical signal is applied to the crystal, the crystal radiates in the thickness, radial, and length dimensions. Usefully, the frequency of the ultrasound signal applied matches the resonance frequency which optimizes radial vibration. As is best illustrated in FIG. 6, vibration results in acoustic pressure radiating outwardly toward a balloon 58 and a target tissue 60, and inwardly toward gap 54. Ultrasonic acoustic pressure waves do not travel through low density materials; they are reflected by low density materials. Since gap 54, according to one embodiment of the present invention, contains a low density material, the acoustic pressure waves which radiate inwardly are reflected, rather than being absorbed by the catheter. The reflected pressure waves then radiate outwardly toward balloon 58 and target tissue 60, resulting in increased energy available for the transport of therapeutic substances. The increase in energy available for transport of therapeutic substances is achieved without a concomitant increase in transducer size, or increase in power supplied to the transducer. Incorporating gap 54 into the design also permits the use of a smaller transducer for a given desired energy level, which results in a smaller catheter profile, enhancing maneuverability through body passageways. In addition, more energy can be applied to the crystal without causing the temperature of the crystal to increase.

Referring again to FIG. 5A, an electrical lead 56 is a coaxial cable and electrically connects transducer 42 to an electrical power supply (not shown) via delivery/electrical lumen 32. The coaxial cable contains an inner wire for carrying the electrical signal, and a ground wire surrounding the inner wire to shield the inner wire from electrical noise. The coaxial cable must be used in lieu of a twisted pair or bare wire in order to minimize impedance loss over the length of the wire.

In one embodiment, balloon 58 is incorporated at the distal end of the catheter, in fluid communication with delivery/electrical lumen 32, through which a therapeutic substance is delivered, as illustrated in FIG. 5A. Balloon 58 can be made from a membrane having pores, and is inflated by introduction of the therapeutic substance through delivery/electrical lumen 32. The pressure of the therapeutic substance within balloon 58 causes balloon 58 to dilate from a collapsed configuration to an expanded configuration, wherein the outer surface of the balloon wall is compressed against the inner surface of passageway 40. The pressure inside balloon 58 is usefully not great enough to cause more than a minimal amount of therapeutic substance to escape from balloon 58. Vibrating transducer 42 supplies acoustic pressure to assist in transport of the therapeutic substance through balloon 58 and into the surrounding target tissue 60. The therapeutic substance can then be delivered from balloon 58 to the treatment area, via ultrasonic energy provided by the transducer 42.

Balloon 58 can be microporous, i.e., having many pores of smaller diameter. By way of example, and not limitation, a microporous membrane could contain $10^6$ pores having a diameter ranging from about 0.3 μm to about 2.5 μm. Alternatively balloon 58, can be macroporous, i.e., having fewer pores of larger diameter. By way of example, and not limitation, a macroporous balloon could have 100 pores with a 25 µm diameter. Suitable membrane materials include polyester, polyolefin, fluoropolymer, and polyamide. The membrane thickness should be less than 0.005 inches, and in any event, due to the physics of ultrasound, should be less than or equal to ¼ of the driving ultrasound wavelength.

Perfusion holes 62 can be incorporated on guidewire/perfusion lumen 34, which allow blood to continue to flow past balloon 58 which would otherwise occlude flow when balloon 58 is expanded, and simultaneously cool transducer 42. Providing continued blood flow during treatment allows longer treatment times.

In lieu of having a porous balloon, in an alternative embodiment illustrated in FIG. 5B, a sealing balloon 64 can be mounted on distal portion 44 of the catheter tube 36 and is inflated by an inflation lumen 66, which can be exterior to guidewire/perfusion lumen 34, to engage the walls of passageway 40. Sealing balloon 64 can be located distal to transducer 42. Sealing balloon 64 may be made of an impermeable expandable material, for example latex, and prevents the therapeutic substance eluted from the distal end of delivery/electrical lumen 32 from being carried off by the downstream flow of the blood. Sealing balloon 64 is kept in position by balloon seal members 68, which, for example, may be laser welded to the catheter distal portion 44, or secured to the catheter distal portion 44 by medical grade adhesive. This embodiment may optionally include perfusion holes 62 on guidewire/perfusion lumen 34 to maintain blood flow across sealing balloon 64, and cool transducer 42, increasing possible treatment time as described earlier. It is contemplated by one of ordinary skill in the art that any suitable combination of the above described embodiments can be used in combination with one another. For example, the combination of both a porous balloon in addition to sealing balloon 64 can be used with any of catheter assemblies 30 of the present invention.

Catheter assembly 30 shown in FIG. 5A may be used for delivery of a therapeutic substance in the following manner. Guidewire 38 is inserted into guidewire/perfusion lumen 34, and the user advances the catheter assembly 30 through the subject's vasculature until transducer 42 is positioned across the intended treatment area. For penetration of the therapeutic substance into the tissue matrix, delivery/electrical lumen 32 is loaded with therapeutic substance, and a voltage is applied to transducer 42 simultaneously via electrical lead 56 contained within delivery/electrical lumen 32. The electrical signal supplied to transducer 42 typically can have a frequency between 200 kHz and 8 MHz, an amplitude between 125V and 250V, a duty cycle between 5% and 10%, and a sweep time between 50 µs and 300 µs. The electrical signal is provided by a frequency generator, for example, Hewlett Packard Model No. HP 3314A, electrically connected to an amplifier, for example, ENI Model 240L.

For penetration of therapeutic substance into cells which form the tissue matrix, the therapeutic substance can be first delivered to the intended treatment area through delivery/electrical lumen 32. An electrical signal is supplied to transducer 42 after the requisite volume of therapeutic substance has passed through the distal end of delivery/electrical lumen 32 and into the intended treatment area. The electrical signal supplied to transducer 42 can have a frequency between 20 kHz and 3 MHz, an amplitude greater than 94.8V, a duty cycle between 5% and 20%, and a sweep time between 5,000 µs and 20,000 µs. Vibrating transducer 42 supplies acoustic pressure which is believed to disrupt individual cell walls, permitting the therapeutic substance to enter target tissue 60.

For diagnostic ultrasound, the electrical signal supplied to transducer 42 can have a frequency between 20 MHz and 40 MHz.

Examples of therapeutic substances or agents that are typically used to treat a subject and are appropriate for use in conjunction with the catheter assembly 30 via delivery/electrical lumen 32 include, for example, antineoplastic, antiinflammatory, antiplatelet, anticoagulants, fribrinolytic, thrombin inhibitor, antimitotic, and antiproliferative substances. Examples of antineoplastics include paclitaxel and docetaxel. Examples of antiplatelets, anticoagulant, fibrinolytics, and thrombin inhibitors include sodium heparin, low molecular weight heparin, hirudin, argatroban, forskolin, vapiprost, prostacyclin and prostacyclin analogues, dextran, D-phe-pro-argchloromethylketone (synthetic antithrombin), dipyridamole, glycoprotein IIb/IIIa platelet membrane receptor antibody, recombinant hirudin, thrombin inhibitor (available from Biogen'), and 7E-3B® (an antiplatelet drug from Centocore). Examples of suitable antimitotic agents include methotrexate, azathioprine, vincristine, vinblastine, flurouracil, adriamycin, and mutamycine. Examples of cytostatic or antiproliferative agents include rapamycin, angiopeptin (a somatostatin analogue from Ibsen), angiotensin converting enzyme inhibitors such as Captopril® (available from Squibb), Cilazapril® (available from Hoffman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), pemirolast potassium and nitric oxide. Other therapeutic substances or agents which may be appropriate include alpha-interferon, genetically engineered epithelial cells, prostaglandins such as PGE-1, and dexamethasone. While the foregoing therapeutic substances or agents are well known for preventative and treatment purposes, the substances or agents are provided by way of example and are not meant to be limiting. Other therapeutic substances which are currently available or that may be developed in the future are equally applicable for use with the present invention. The treatment of patients using the above mentioned medicines is well known to those having ordinary skill in the art.

FIG. 7 illustrates another embodiment of catheter assembly 30 having three transducers 42a, 42b and 42c disposed at distal portion 57 of guidewire/perfusion lumen 34. Each transducer 42a–42c has a proximal end 72 and a distal end 74, which defines the length, $l_3$, of each transducer 42a–42c. Each distal end 74 of transducers 42a and 42b is positioned at a preselected distance $d_1$ from the proximal end 72 of the adjacent transducer.

The length, $l_3$, of each transducer 42a–42c can be of equal or different measurement. To treat an active area in the vasculature of a subject that is about 1 centimeter long (0.395 inches, or 395 "mils"), exemplary length, $l_3$, and distance $d_1$ can be 100 mils and 50 mils, respectively. The number of transducers is not limited to the illustration of FIG. 7, and any suitable number of transducers can be used with this embodiment of the invention.

Transducers 42a–42c are mounted to the distal portion 44 of the catheter with medical grade adhesive. The selected medical grade adhesive is compatible both with the perylene or other compound coating transducers 42a–42c and the material forming the distal portion 57 of guidewire/perfusion lumen 34.

Transducers 42a–42c can be electrically connected in parallel, or in series. Electrically connecting transducers 42a–42c in parallel provides a more consistent electrical signal from crystal to crystal, in part because the resulting voltage drops across inner and outer surfaces 50 and 48 are equal. However, this parallel configuration is more difficult to fabricate than the configuration where transducers 42a–42c are electrically connected in series. Electrical lead 56, a coaxial cable, is electrically connected to a conductive outer surface 76 of proximal transducer 42a, which in turn is electrically connected to the conductive outer surface 76 of adjacent transducer 42b. The electrical connection can be made by insulated magnet wire 78. Electrical connections are repeated along the outer surface 76 of each transducer 42a–42c until distal transducer 42c is reached. Electrical connections are similarly made to connect conductive inner surfaces 80 of each transducer 42a–42c to electrical lead 56. The electrical connections can be made by soldering, welding, or conductive epoxy.

Since transducers 42a–42c are fabricated from, for example, a hard ceramic, transducers 42a–42c are very stiff. Segmenting transducer 42 into transducers 42a–42c permits the user to more easily direct the catheter assembly 30 around curves and corners in the subject's vasculature.

In accordance with another embodiment, illustrated in FIG. 8, inner surface 50 of each transducer 42a–42c is positioned at a preselected distance from outer surface 52 of the distal portion 57 of guidewire/perfusion lumen 34. The preselected distance defines gap 54 between inner surface 50 of transducers 42a–42c and outer surface 52. Gap 54 may contain any suitable low density material, including gaseous substances such as ambient air, oxygen, nitrogen, helium, an open-cell polymeric foam, a closed-cell polymeric foam, or other low density materials. Gap 54 functions to increase available ultrasound energy as described above. Delivery of a therapeutic substance is accomplished as described above under the detailed description for FIG. 5A.

Each transducer 42a–42c has a proximal end 72 and a distal end 74, which defines the length, $l_3$, of each transducer 42a–42c. Each distal end 74 of transducers 42a–42c is positioned at a preselected distance $d_1$ from proximal end 72 of adjacent transducer 42a–42c.

Transducers 42a–42c can be defined by a hollow tubular body having an outer surface 48 and an inner surface 50. Outer surface 48 and inner surface 50 can be coated conformally with perylene or a similar compound. Anchoring points 46 are formed from medical grade adhesives. The selected choice of medical grade adhesive should be mutually compatible both with the coating and the material forming distal end 57 of catheter assembly 30. Anchoring points 46 should act as standoffs to separate inner surface 50 of transducers 42a–42c from outer surface 52 of guidewire/perfusion lumen 34, thereby creating gap 54.

The length, $l_3$, of each transducer 42a–42c can be of equal or different measurement. To treat an active area in the vasculature of a subject that is about 1 centimeter long (0.395 inches, or 395 "mils"), exemplary length, $l_3$, and distance $d_1$ can be 100 mils and 50 mils, respectively. The number of transducers is not limited to the illustration of FIG. 8, and any suitable number of transducers can be used with this embodiment of the invention.

While particular embodiments of the invention have been shown and described, it will be obvious to those skilled in the art that modifications, combinations, and substitutions can be made without departing from the invention in its broader aspects. For example, the embodiment described in FIG. 5A could be modified so that a sealing balloon is positioned distal or proximal to a plurality of transducers, rather than a single transducer. Similarly, a sealing balloon could be positioned distal or proximal to a plurality of transducers that are disposed within a balloon themselves. Therefore, the appended claims are to encompass within their scope all such changes and modifications as fall within the true spirit and scope of this invention.

The invention claimed is:

1. A method for delivering a therapeutic substance to an internal body tissue target area comprising the acts of:
   (a) providing a catheter having a distal end and a proximal end, and further having a delivery lumen, said delivery lumen extending from the distal end of the catheter to the proximal end of the catheter for delivery of a therapeutic substance;
   (b) further providing a transducer, for creating an energy, supported at the distal end of the catheter by a number of anchoring points, wherein an inner surface of the transducer is positioned at a distance from an outer surface of the catheter, the distance defining a gap between the outer surface of the catheter and the inner surface of the transducer, the gap containing a low density material for reflecting the energy from the gap towards the target area, wherein the anchoring points comprise an adhesive that seals the gap at a distal end and proximal end of the gap;
   (c) positioning said catheter proximate the internal body tissue target area;
   (d) causing a therapeutic substance to elute from the delivery lumen at the distal end of the catheter; and
   (e) transmitting an electrical signal to the transducer for creating the energy.

2. The method of claim 1, wherein the therapeutic substance is selected from a group consisting of antineoplastic, antiinflammatory, antiplatelet, anticoagulant, fibrinolytic, thrombin inhibitor, antimitotic, and antiproliferative substances and mixtures thereof.

3. A method of treating an internal body tissue with a therapeutic substance comprising:
   (a) locally delivering the therapeutic substance in the vicinity of the internal body tissue;
   (b) generating ultrasonic energy in the vicinity of the internal body tissue, wherein the ultrasonic energy is generated by a transducer;
   (c) adjusting the ultrasonic energy by manipulating an electronic signal applied to the transducer, wherein the electronic signal is oscillated approximately equal to the mechanical resonance frequency of the transducer; and
   (d) amplifying the ultrasonic energy by interposing a gap between a catheter for delivering the therapeutic substance and the transducer for generating the ultrasonic energy, wherein the gap is sealed by an adhesive at a distal end and proximal end of the gap.

4. The method of claim 1, wherein the electrical signal has a frequency greater than about 20 kHz.

5. The method of claim 1, wherein the electrical signal has a voltage greater than about 94.8 V.

6. The method of claim 3, wherein the electrical signal has a frequency greater than about 20 kHz.

7. The method of claim 3, wherein the electrical signal has a voltage greater than about 94.8 V.

* * * * *